United States Patent [19]

Saklikar et al.

[11] Patent Number: 5,294,891

[45] Date of Patent: Mar. 15, 1994

[54] METHOD AND APPARATUS FOR DETERMINING THE QUALITY OF A COLLOIDAL SUSPENSION

[75] Inventors: Arvind R. Saklikar, Sunnyvale; William A. Lloyd, Plymouth, both of Calif.

[73] Assignee: PowerPrint Technologies, Inc., Sunnyvale, Calif.

[21] Appl. No.: 32,374

[22] Filed: Mar. 18, 1993

[51] Int. Cl.$^5$ .............................................. G01R 27/14
[52] U.S. Cl. ................................ 324/705; 324/709; 324/713; 324/452
[58] Field of Search ............... 324/452, 453, 457, 458, 324/705, 709, 713, 715, 718

[56] References Cited

U.S. PATENT DOCUMENTS

| | | | |
|---|---|---|---|
| 3,358,223 | 12/1967 | Birnstingl | 324/705 |
| 3,669,073 | 6/1972 | Savit et al. | 118/637 |
| 4,398,145 | 8/1983 | Quayle | 324/705 |
| 4,497,208 | 2/1985 | Oja et al. | 73/584 |
| 4,499,766 | 2/1985 | Fathauer et al. | 73/304 |
| 4,499,767 | 2/1985 | Fathauer et al. | 73/304 |
| 4,552,019 | 11/1985 | Freeman | 73/584 |
| 4,663,265 | 5/1987 | Uytterhoeven et al. | 430/114 |
| 4,837,501 | 6/1989 | Fry et al. | 324/709 |
| 4,907,442 | 3/1990 | Jones et al. | 73/38 |
| 4,907,453 | 3/1990 | Marlow et al. | 73/584 |
| 5,068,618 | 11/1991 | Fry et al. | 324/706 |
| 5,140,527 | 8/1992 | Jones et al. | 364/499 |

OTHER PUBLICATIONS

Emma H. B. DeLacey, et al., "Dielectric Response and Conductivity of Dilute Suspensions of Colloidal Particles", J. Chem. Soc., Faraday Trans. Feb. 2, 1981, 77, pp. 2007–2039.

S. Stotz, "Particle Charge and Stability of Liquid Developers in Electrophotography," Current Problems in Electrophotography edited W. F. Berg and K. Hauffe, Jan. 1989, pp. 336–346.

*Primary Examiner*—Kenneth A. Wieder
*Assistant Examiner*—Glenn Brown
*Attorney, Agent, or Firm*—Phong K. Truong; Dennis S. Fernandez

[57] ABSTRACT

A method and apparatus for determining the quality of a colloidal suspension. According to the method of the present invention, an oscillating input electrical signal is applied simultaneously to a sample of the colloidal suspension to be tested and to a reference solution. The reference solution is substantially identical to the colloidal suspension except that the colloidal particles have been removed. The input signal causes charge particles and molecules within both substances to move, thereby, giving rise to electrical currents. Thus, a test current is extracted from the colloidal suspension and a reference current is extracted from the reference solution. Thereafter, a differential output current is derived by substracting the reference current from the test current. The peak-to-peak magnitude of the differential output current is measured, and the phase of the output current is compared to the phase of the input signal to determine the difference in phase between the two signals. Based on the peak-to-peak value and the phase difference, the quality of the colloidal suspension is determined.

24 Claims, 6 Drawing Sheets

METHOD AND APPARATUS FOR DETERMINING THE QUALITY OF A COLLOIDAL SUSPENSION

FIELD OF THE INVENTION

This invention relates to colloidal suspensions and more specifically to a method and apparatus for determining the quality of a colloidal suspension.

BACKGROUND ART

Colloidal suspensions, such as paints, blood plasma, and certain foods, typically comprise a plurality of colloidal particles dispersed throughout a continuous liquid or gaseous medium. A particular type of colloidal suspension which has found important application in recent years is that of liquid toner used in electrostatic and electrographic plotters and printers. Liquid toner is typically composed of a liquid solvent, a charge control agent, and a plurality of toner particles dispersed throughout the solvent. The charge control agent is included in the suspension for the purpose of imparting to the toner particles the charge needed by the particles to deposit onto a charged surface such as a statically charged piece of paper. As the liquid toner is used for printing purposes, the toner particles are progressively depleted, leaving behind only the charge control agent and the solvent. Once the concentration of toner particles falls below a certain level, the liquid toner becomes ineffective and must either be replaced or be replenished with additional toner particles. From this discussion, it is clear that the effectiveness and, hence, the quality of the liquid toner is based upon the concentration of the toner particles. For best results, an optimal ratio should be maintained between the concentration of the toner particles and the molecular concentration of the suspension agent including the solvent and the charge control agent.

Since the quality of a liquid toner is mainly a function of the toner particle concentration, an effective method and apparatus for testing the quality of the toner should provide a clear indication of the toner concentration. The prior art, however, fails to provide a method or a means for satisfactorily determining the quality of a liquid toner or a colloidal suspension in general. The prior art teaches a method for measuring the electrokinetic properties of a colloidal suspension (U.S. Pat. No. 4,497,208), a method for measuring the potential of colloidal particles in a colloidal suspension (U.S. Pat. No. 4,552,019), and a method for measuring the electrical conductivity of a colloidal suspension (U.S. Pat. No. 4,907,453). The measurements of electro-kinetic properties, potentials, and conductivity, however, do not provide a good indication of the toner particle concentration, and hence, fail to give an accurate indication of the quality of a liquid toner. Hence, a need exists for an effective method and apparatus for determining the quality of a liquid toner and a colloidal suspension in general.

SUMMARY OF THE INVENTION

In accordance with the present invention, a method is provided for determining the quality of a colloidal suspension, wherein an oscillating input electrical signal, preferably having a frequency between about 1 Hz and 10 Hz, is applied to the colloidal suspension to be tested, and a first output current is extracted from the colloidal suspension. At the same time, the input signal is also applied to a reference solution which is substantially identical to the colloidal suspension except that the colloidal particles have been removed, and a second output current is extracted from the reference solution. Thereafter, a differential output current is derived by subtracting the second output current from the first. Once this differential output current is obtained, its magnitude or peak-to-peak value is measured, and its phase is compared to that of the input signal to determine whether there is a phase difference or phase shift between the two signals. Based on the peak-to-peak value of the differential output current and the degree of the phase shift, the concentration of the toner particles and, thus, the quality of the colloidal suspension is determined.

The present invention also provides an apparatus for implementing the aforementioned method. The apparatus comprises an oscillating signal source, a test cell, a reference cell, a differential amplifier, a phase detector and a magnitude detector. The signal source generates an oscillating input electrical signal which is applied simultaneously to both the test cell and the reference cell. The test cell houses the colloidal suspension to be tested and has an input electrode for receiving the input signal, and an output electrode for providing a first output current. The reference cell houses the reference solution mentioned above and has an input electrode for receiving the input signal, and an output electrode for providing a second output current. The differential amplifier receives the first and second output currents as inputs and provides as output a differential output current which represents the difference between the first and second output currents. The magnitude detector measures the magnitude or peak to-peak value of the differential output current, and the phase detector compares the phase of the differential current to the phase of the input signal to determine the phase shift between the two signals. The apparatus of the present invention thus provides the magnitude and the phase shift needed to determine the quality of the colloidal suspension.

DETAILED DESCRIPTION OF THE PREFERRED EMBODIMENTS

Figure 1:
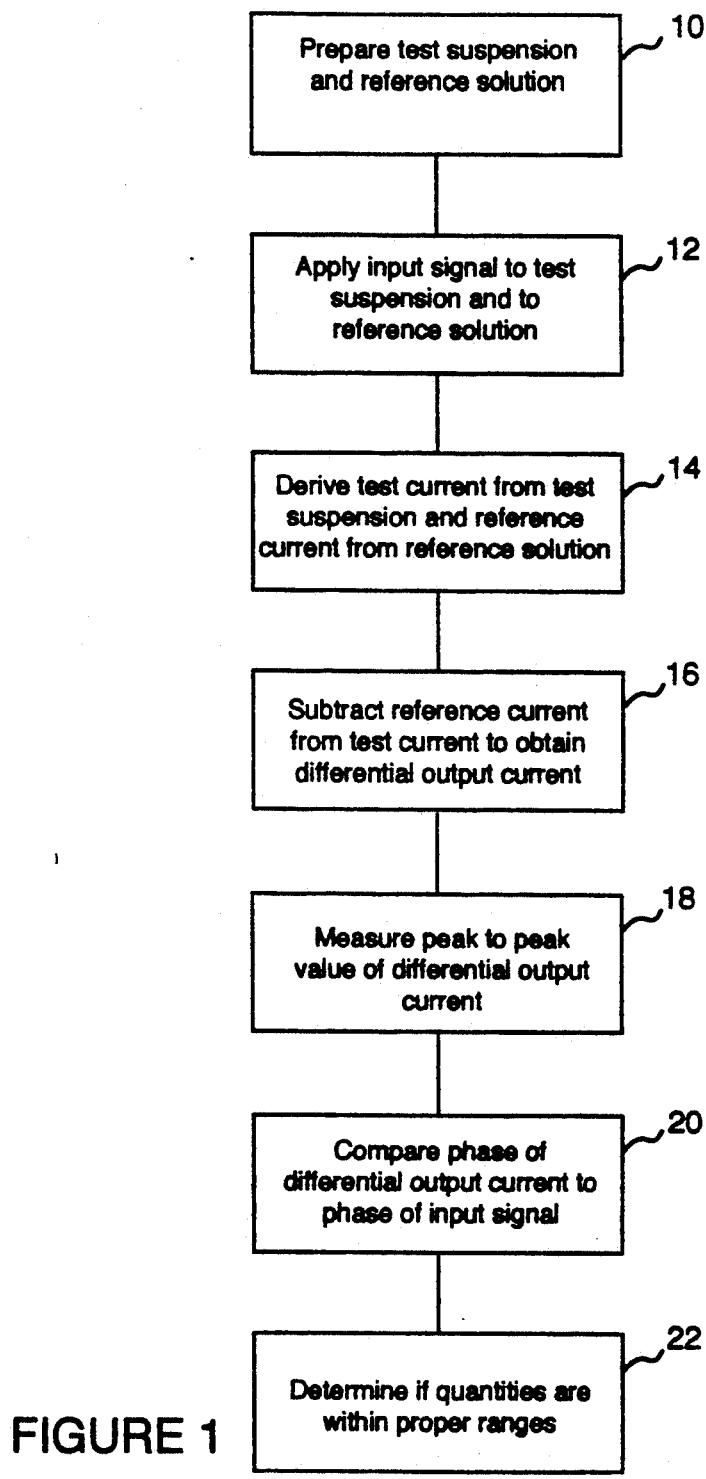
FIG. 1 is a flow diagram of the method of the present invention.

Before proceeding to describe the method and apparatus of the present invention, the theoretical considerations underlying the invention will first be discussed. For the sake of illustration, the following discussion is directed at liquid toner suspensions, but it should be noted that the discussion applies to other colloidal suspensions as well.

A liquid toner typically consists of a liquid solvent, a charge control agent, and a plurality of toner particles dispersed throughout the solvent. By definition, suspended particles within a colloidal suspension have a charge with respect to the suspension medium; thus, the toner particles have a charge with respect to the solvent. Consequently, when liquid toner is excited by an oscillating electrical signal, the toner particles move through the solvent, thereby, creating an oscillating electrical current. The application of an electrical signal causes more than just the toner particles to move, however, because the charge control agent molecules also have a charge and, hence, will also move in response to the excitation signal. Consequently, the current which results from the application of an electrical signal has both a toner particle component and a charge control agent component. The resultant current (i) is expressed by the following equation:

$$i = n_1 q_1 u_1 \sin w_1 t + n_2 q_2 u_2 \sin w_2 t$$

where
- $n_1$ = the number of toner particles;
- $q_1$ = the charge on the toner particles;
- $u_1$ = the velocity of the toner particles; and
- $w_1$ = the resultant phase shift in the toner particle current due to drag on the particles; and where
- $n_2$ = the number of charge control agent molecules;
- $q_2$ = the charge on the charge control agent molecules;
- $u_2$ = the velocity of the charge control agent molecules; and
- $w_2$ = the resultant phase shift in the charge control molecule current due to drag on the molecules.

From the above equation, it is clear that the resultant current (i) has as a component the current due to the movement of the charge control agent molecules. However, for the purpose of determining the quality of a liquid toner, only the toner particle current is of interest. Hence, the control agent molecule current needs to be subtracted from the total current to isolate the toner particle current.

Once isolated, the toner particle current provides useful information as to the quality of the liquid toner. First, the magnitude or peak-to-peak value of the current provides an indication of the conductivity of the toner due to both the toner particles and the control agent molecules. If the peak-to-peak value exceeds a certain level, then it is known that the concentration of either the toner particles or the control agent molecules is too high for the liquid toner to be usable. Likewise, if the peak-to-peak value falls below a certain level, the concentration of either the toner particles or the control agent molecules is too low for the liquid toner to be effective. Thus, the peak-to-peak value gives an indication of the relative concentrations of the toner particles and the control agent molecules.

The phase difference or phase shift between the toner particle current and the excitation signal also provides important information regarding the quality of the liquid toner. The phase shift is directly proportional to the amount of charge in the suspension. Since the amount of charge is directly proportional to the number of toner particles in the suspension, the phase shift is therefore directly proportional to the number of toner particles in the suspension. The greater the concentration of toner particles, the greater the phase shift. Therefore, the phase shift provides a direct indication of the toner particle concentration.

Together, the peak-to-peak value and the phase shift define the quality of the liquid toner. Where both quantities are within proper operating limits, the liquid toner quality is good and the toner may be used for printing purposes. Where either quantity is beyond the proper operating range, the liquid toner must either be replaced or refreshed.

With these theoretical considerations in mind, the method and apparatus of the present invention will now be described. With reference to FIG. 1, there is shown a flow diagram of the method of the present invention, wherein the first step of the method is to prepare 10 a test sample and a reference solution. The test sample is prepared simply by taking a sample from the liquid toner to be tested, but the reference solution is derived. The reference solution may be derived by taking a sample of the liquid toner to be tested and removing the toner particles from the toner, either by centrifuging the sample toner or by plating out the toner particles. Both centrifuging and plating out are techniques well known in the art and need not be elaborated upon herein. The reference solution, therefore, is substantially identical to the liquid toner except that the toner particles have been removed. Hence, the reference solution contains only the solvent and the charge control agent. The significance of the reference solution will become apparent as the method of the present invention is described further.

Once the test sample and reference solution have been prepared, an oscillating input electrical signal, preferably having a frequency between 1 Hz and 10 Hz, is applied 12 to each of the solutions. Because the test sample has toner particles and charge control agent molecules, the application of the input signal causes the particles and molecules to move with the varying electric field created by the input signal, thereby, giving rise to an oscillating electric current. This test current is extracted 14 from the test sample. Likewise, the application of the input signal 12 causes the charge control agent molecules within the reference solution to move, thus, inducing a reference current which may be extracted 14 from the reference solution.

The test current from the test sample has two components: a toner particle component; and a charge control agent component. As discussed above, it is necessary to isolate the toner particle component if the quality of the test sample is to be determined. Thus, the charge control agent component needs to be subtracted from the total test current. This may be achieved by subtracting 16 the reference current from the test current. Recall that the reference solution contains no toner particles so that the reference current is attributable entirely to the movement of the charge control agent molecules. By subtracting 16 the reference current from the test current, the charge control agent current components are made to cancel each other out, thus leaving only the toner particle component of the test current. This current, referred to herein as the differential output current, is the current used to determine the quality of the test sample.

Once the differential output current is derived, its magnitude or peak-to-peak value is measured 18. In addition, its phase is compared 20 to the phase of the input signal to determine the phase shift between the two signals. The peak-to-peak value and the phase shift are then analyzed 22 to determine if they are both within their proper operating ranges. If they are, then the toner is still effective and may continue to be used. The operating ranges are experimentally derived and will vary from suspension to suspension, but regardless of the colloidal suspension, the method of the present invention will provide a clear indication of the quality of the toner, in contrast to the methods of the prior art.

Figure 2:
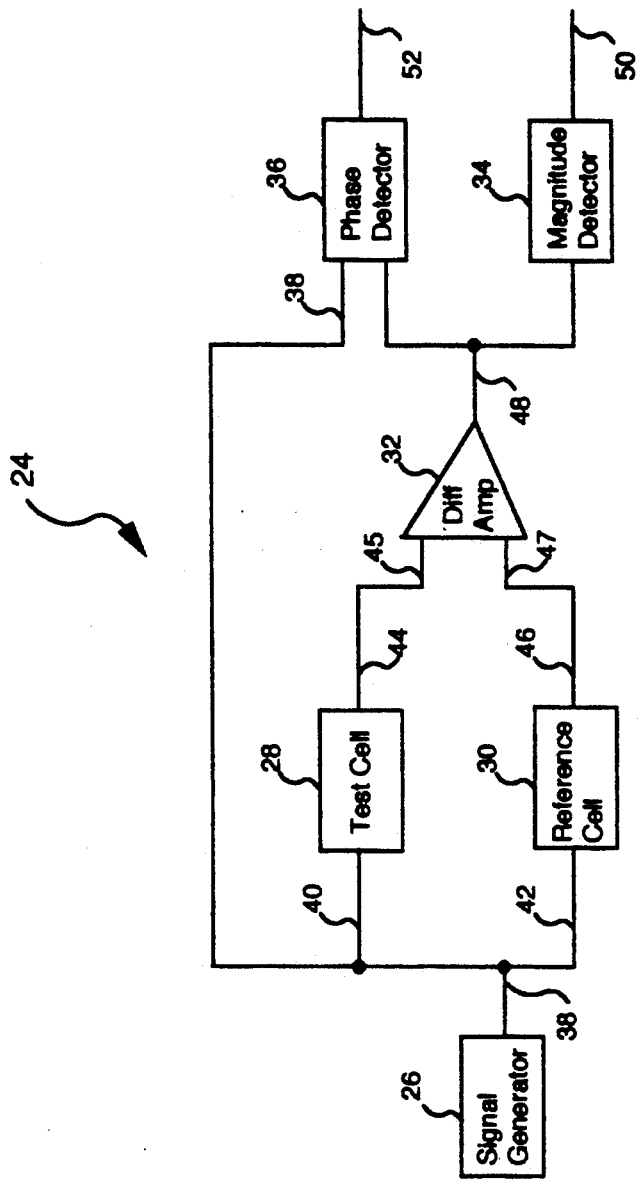
FIG. 2 is a functional block diagram of the apparatus of the present invention.

With reference to FIG. 2, there is shown a functional block diagram of an apparatus for implementing the method of the present invention, wherein the apparatus 24 comprises signal generator 26, test cell 28 for housing a sample of the liquid toner to be tested, reference cell 30 for housing the reference solution, differential amplifier 32, magnitude detector 34, and phase detector 36. The signal generator 26, differential amplifier 32, magnitude detector 34, and phase detector 36 are all of standard construction and are commercially available; thus, only their function and not their construction will be described herein.

The signal generator 26 generates an oscillating input electrical signal 38 which is applied to test cell 28 through input electrode 40, and to reference cell 30 through input electrode 42. Preferably, signal 38 is a low frequency signal having a frequency between about 1 Hz and 10 Hz. In response to the oscillating input signal 38, the toner particles and charge control agent molecules in the liquid toner housed within the test cell 28 move with the varying electric field induced by the input signal 38. Hence, an oscillating electric current, referred to herein as the test current, is induced in the test cell 28, and this test current 45 is extracted from the test cell 28 through output electrode 44. Similarly, the charge control agent molecules in the reference solution housed within the reference cell 30 move in response to the input signal 38, thus, giving rise to a reference current 47. The reference current 47 is extracted from the reference cell through output electrode 46.

The differential amplifier 32 receives as inputs the test current 45 and the reference current 47. Amplifier 32 provides as output a differential output current 48 which represents the difference between the two input currents 45, 7. In effect, amplifier 32 subtracts the reference current 47 from the test current 45 to isolate the toner particle component of the test current 45.

Thereafter, differential output current 48 is sent to the input of magnitude detector 34, and in response, detector 4 provides an output 50 which is indicative of the peak-to-peak magnitude of the differential output current 48. Current 8 is also sent, along with the input signal 38, to the inputs of the phase detector 36. Detector 36 compares the phase of current 48 with the phase of signal 38 and provides an output 2 which gives an indication of the phase difference or phase shift between the two input signals 38, 48. The two quantities, peak-to-peak value and phase shift, needed to determine the quality of the test toner are thus provided by the apparatus 24.

Figure 3:
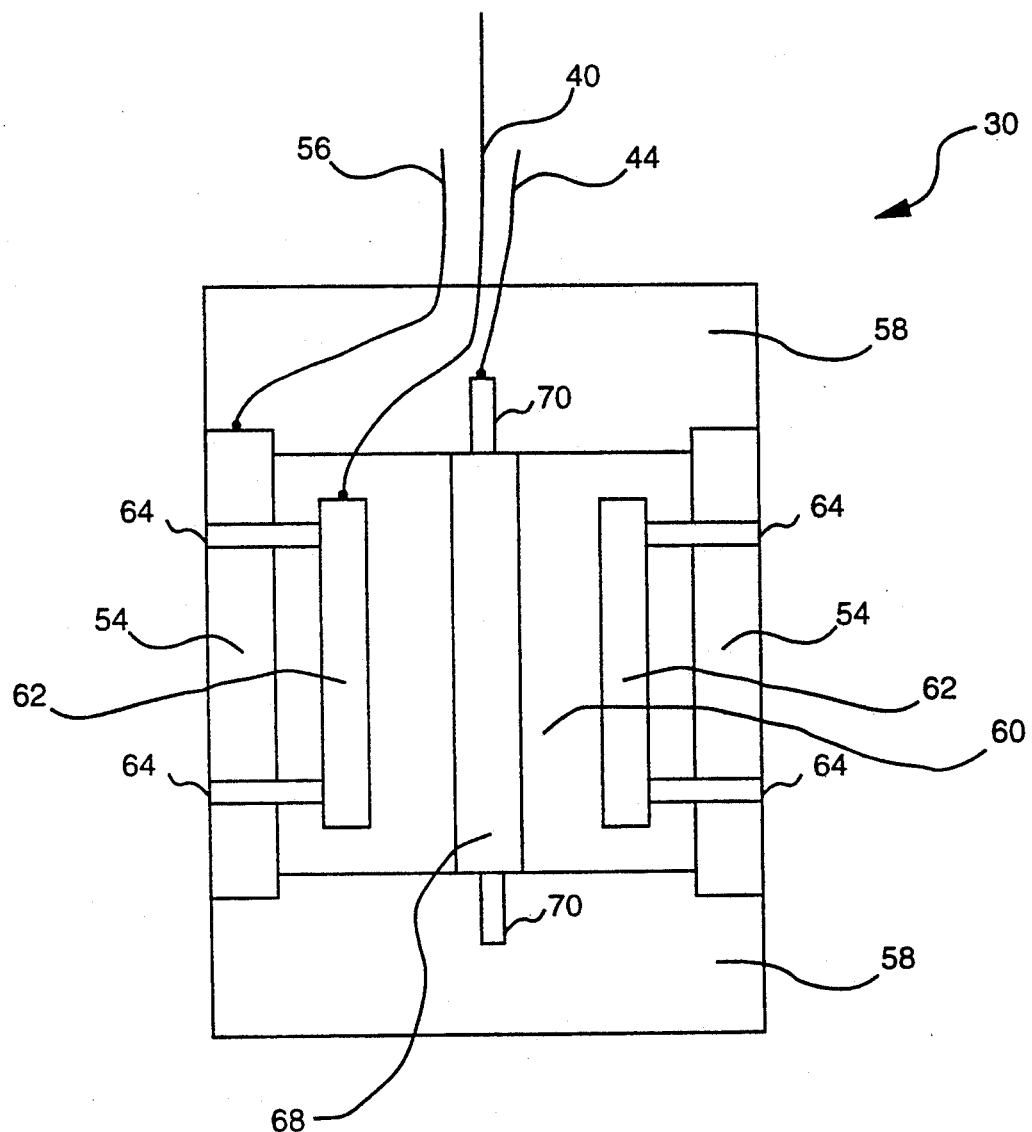
FIG. 3 is a cross-sectional view of a reference cell in accordance with a first preferred embodiment of the apparatus of the present invention.

The test cell 28 and reference cell 30 of apparatus 24 will now be described in greater detail. In accordance with a first preferred embodiment of the apparatus 24 of the present invention, reference cell 30 takes the form shown in FIG. 3 and test cell 28 takes the form shown in FIG. 4. With reference to FIG. 3, a cross-sectional view of the reference cell 30 is provided, wherein the reference cell 30 comprises a cylindrical casing 54 having two open ends. Casing 54 preferably is constructed of a suitable grade of stainless steel such that it is chemically inert and behaves as an electrical shield to reduce noise in the overall apparatus. Welded to casing 54 is wire 56 which connects the casing to ground. Each end of the casing 54 is closed off by a plastic end cap 58 to hold the reference solution 60 within the casing 54.

Reference cell 30 also comprises a first active electrode 62 which preferably takes the form of a stainless steel cylindrical pipe. Electrode 62 is attached to the casing 54 by Nylon set screws 64 such that electrode 62 is concentric with the casing 54. Preferably, electrode 62 does not contact either of the end caps 58 to prevent the introduction of electrical noise by the end caps 58. Welded to electrode 62 is wire 40 which receives the input signal from the signal generator. Thus, electrode 62 functions as the input electrode.

Reference cell 30 further comprises electrode 68 which preferably takes the form of a stainless steel bar. Electrode 68 is attached at each end to one of the end caps 58 by way of conductive support 70, and is preferably positioned such that it is concentric with the input electrode 62 and the casing 54. Wire 44, which is used as the output wire, is welded to electrode 68 so that electrode 68 serves as the output electrode.

Figure 4:
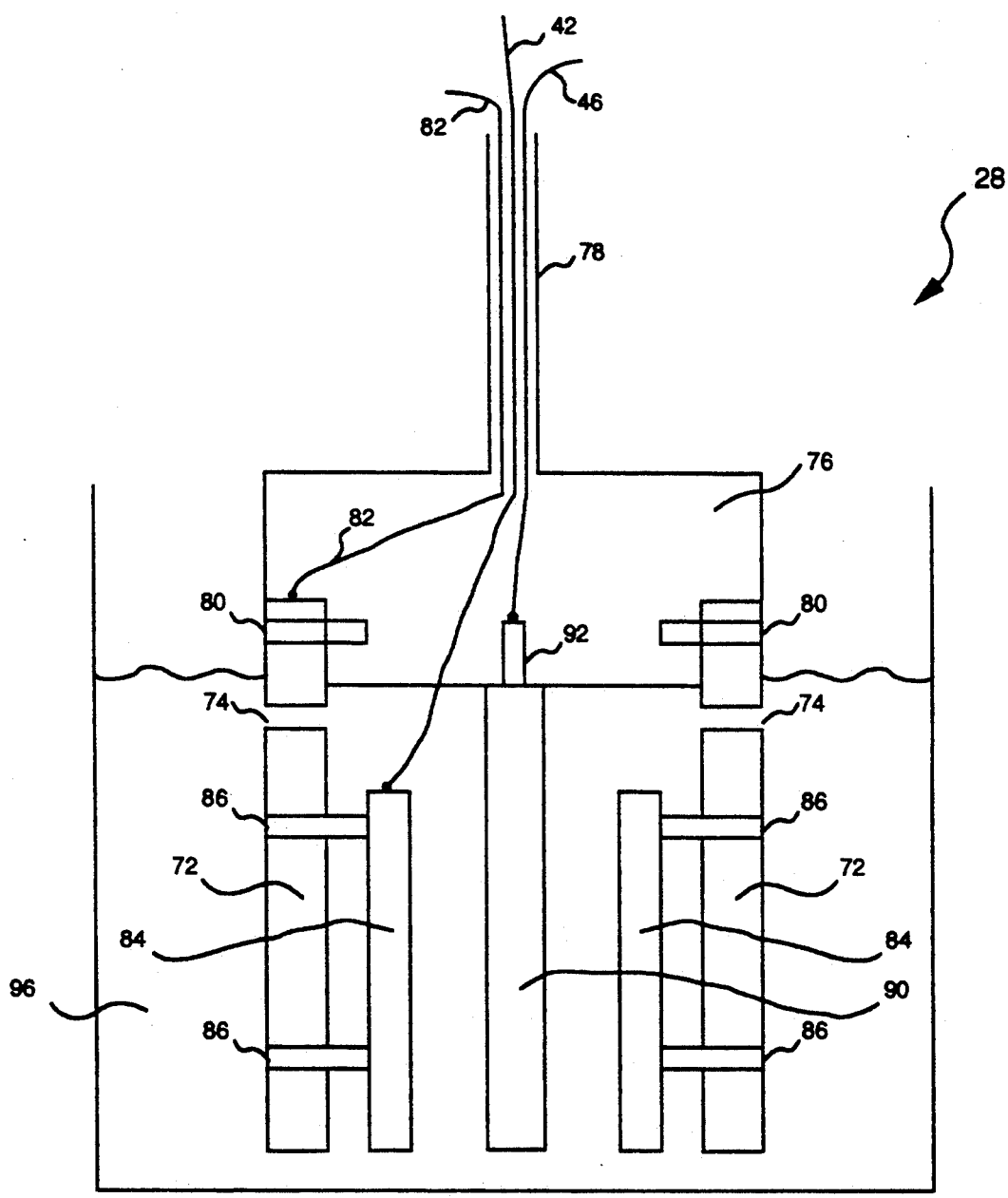
FIG. 4 is a cross-sectional view of a test cell in accordance with a first preferred embodiment of the apparatus of the present invention.

With reference to FIG. 4, there is shown a cross-sectional view of the test cell 28 of the first preferred embodiment. Test cell 28 comprises a stainless steel cylindrical casing 72 having two open ends and a plurality of holes 74 bored through the side of the casing 72. Casing 72 preferably is constructed of the same material and has the same diameter and length as the casing 54 in the reference cell in FIG. 3. One end of the casing 72 is left open while the other end is closed off by a plastic end cap 76 having a long, hollow extension 78 for accommodating a plurality of wires. The casing 72 is securely fastened to the end cap 76 by Nylon set screws 80. Grounding wire 82 is welded to casing 72 to connect the casing to ground.

Test cell 28 also comprises a stainless steel cylindrical pipe electrode 84 which is attached to the casing 72 by way of Nylon set screws 86 in such a manner that the electrode 84 is concentric with the casing 72. Preferably, electrode 84 is made of the same material and has the same dimensions as the electrode 62 in the reference cell of FIG. 3. Electrode 84 preferably does not contact the end cap 76 to prevent the introduction of any electrical noise. Wire 42, which receives the input signal, is welded to electrode 84, thereby, making electrode 84 the input electrode.

Test cell 28 further comprises a stainless steel bar electrode 90 having one end attached to end cap 76 by way of conductive support 92. Electrode 90 is preferably positioned such that it is concentric with electrode 84 and casing 72. Again, it is preferable that electrode 90 be made of the same material and have the same dimensions as electrode 68 in the reference cell 30 of FIG. 3. Welded to conductive support 92 is output wire 46 which allows electrode 90 to function as the output electrode.

In use, the test cell 28 is placed within a reservoir 96 containing the liquid toner to be tested, and submerged until the level of the toner is above the holes 74 in the casing. This fills the test cell 28 with the liquid toner and allows the toner to be tested by the test cell. When reference cell 30 and test cell 28 are used in the apparatus of FIG. 2, the apparatus 24 is said to operate in the static or stand alone mode.

Figure 5:
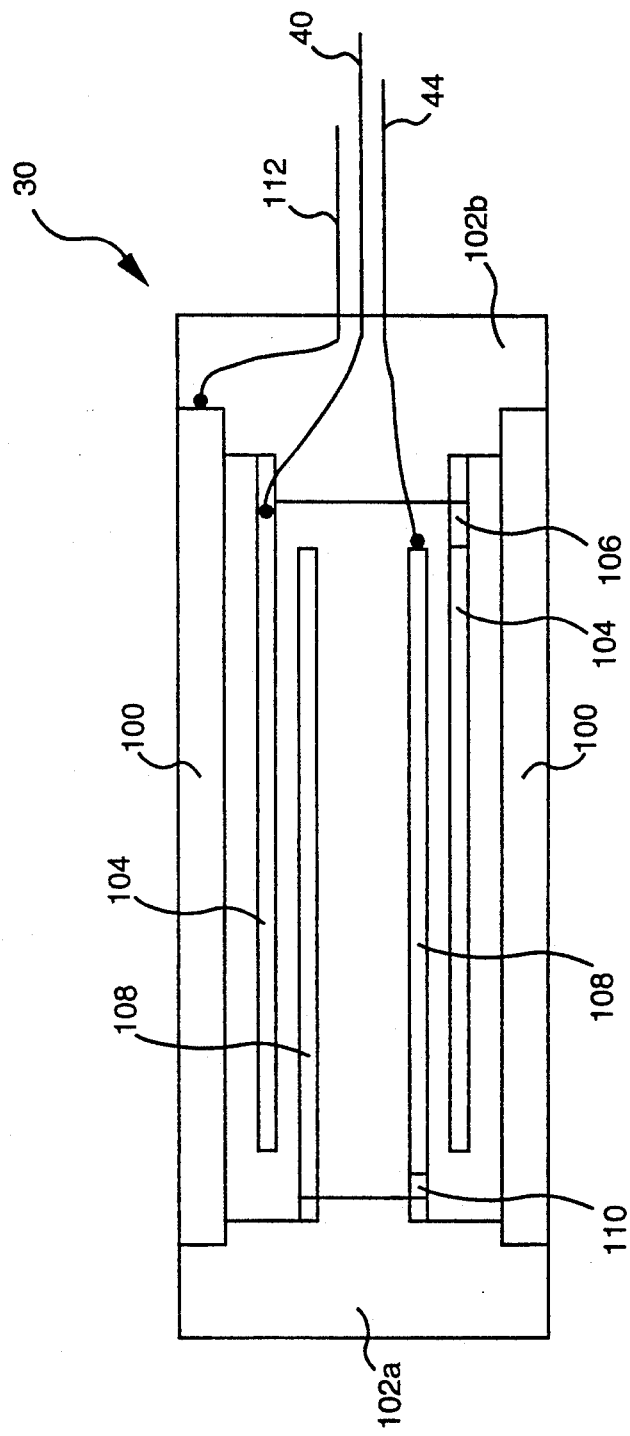
FIG. 5 is a cross-sectional view of a reference cell in accordance with a second preferred embodiment of the apparatus of the present invention.
Figure 6:
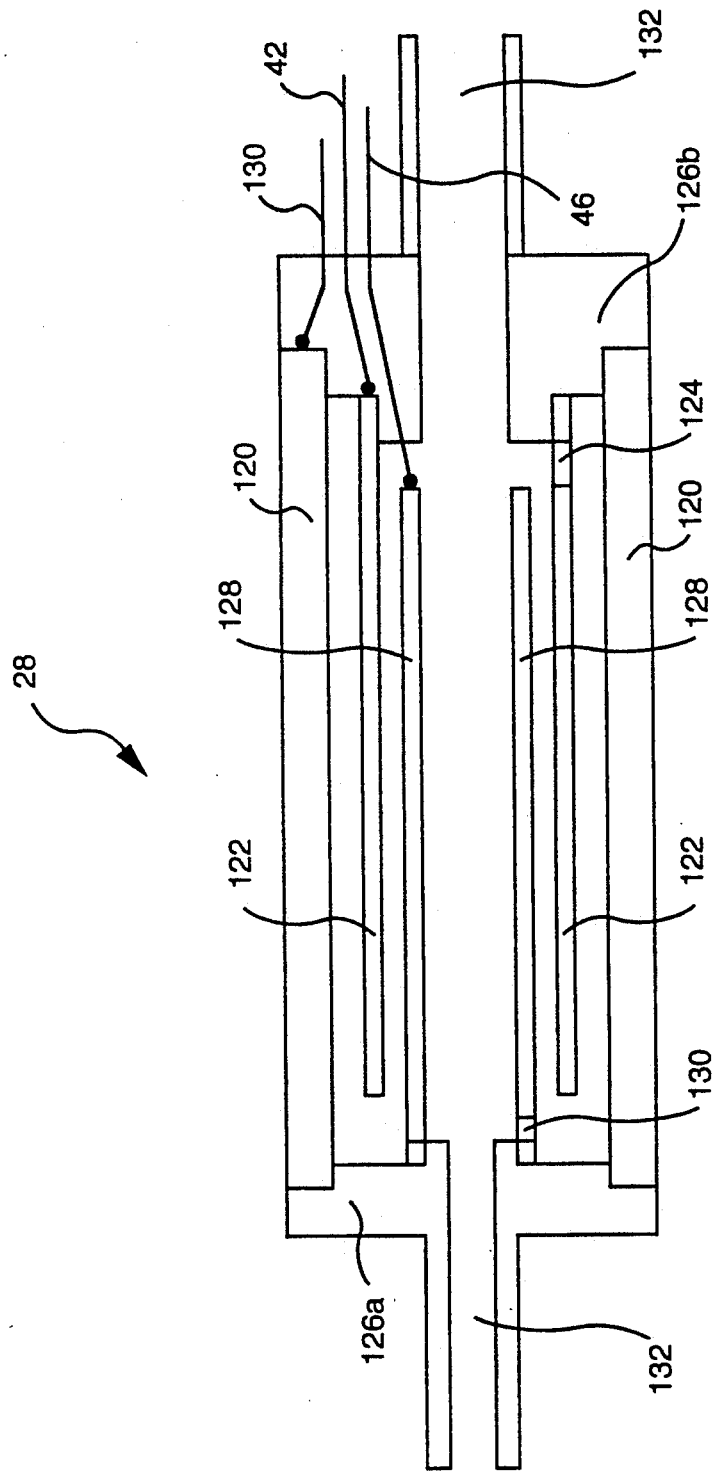
FIG. 6 is a cross-sectional view of a test cell in accordance with a second preferred embodiment of the apparatus of the present invention.

In accordance with a second preferred embodiment of the apparatus 24 of the present invention, reference cell 30 takes the form shown in FIG. 5 and test cell 28 takes the form shown in FIG. 6. When these cells are used in the apparatus of FIG. 2, the apparatus is said to operate in the dynamic mode.

With reference to FIG. 5, which provides a cross-sectional view of the reference cell of the second preferred embodiment, the reference cell 30 comprises a stainless steel cylindrical casing 100 having two open ends, each end being closed off with a plastic end cap 102a, 102b to hold the reference solution within the casing 100. Reference cell 30 also comprises a first stainless steel cylindrical pipe electrode 104 having one end glued to end cap 102b. Preferably, electrode 104 is positioned such that it is concentric with the casing 100, and such that it does not come into contact with the opposite end cap 102a. Also, electrode 104 preferably has a hole 106 bored into its side to allow the reference solution to flow freely within the cell. Reference cell 30 further comprises a second stainless steel cylindrical pipe electrode 108 having one end glued to end cap 102a. Electrode 108 is positioned concentrically with respect to both electrode 104 and casing 100. As with the first electrode 104, electrode 108 preferably does not contact the opposite end cap 102b, and preferably has a hole 110 bored into its side to allow the reference solution to flow freely. Ground wire 112, input wire 40, and output wire 44 are welded to casing 100, electrode 104, and electrode 108, respectively. Thus, electrode 104 functions as the input electrode and electrode 108 serves as the output electrode.

With reference to FIG. 6, there is shown a cross-sectional view of the test cell of the second preferred embodiment. In almost all respects, the test cell 28 is identical to the reference cell shown in FIG. 5. Like reference cell 30, test cell 28 comprises a stainless steel cylindrical casing 120, a first stainless steel cylindrical pipe electrode 122 having one end glued to an end cap 126b, and a second stainless steel cylindrical pipe electrode 130 having one end glued to the other end cap 126a. Preferably, casing 120 and electrodes 122 and 128 are constructed of the same material and have the same dimensions as the corresponding elements in the reference cell 30 of FIG. 5. Electrodes 124 and 130 each has a hole bored into its side to allow the test toner to flow freely through the cell, and Casing 120, electrode 122, and electrode 128 are welded to ground wire 130, input wire 42, and output wire 46, respectively, just as in the reference cell 30 of FIG. 5. The only difference between the two cells 30, 28 is that the test cell 28 is only partially covered by the end covers 126a, 126b. Each of the end covers 126a, 126b in the test cell 28 has a hollow extended portion 132 which extends away from the cell. These hollow extensions 132 allow the test cell 28 to be connected to the plumbing system (now shown) of a printer or plotter which uses liquid toner. Thus, liquid toner flows through the test cell 24 as the toner is being used by the printer pr plotter. Consequently, test cell 28 can be used to test the quality of liquid toner as the toner is being used. For this reason, when the reference and test cells shown in FIGS. 5 and 6, respectively, are used in the apparatus of FIG. 2, the apparatus 24 is said to be operating in the dynamic mode.

What is claimed is:

1. For a colloidal suspension having colloidal particles dispersed throughout a continuous medium, a method for determining the quality of said colloidal suspension, comprising the steps of:

applying an oscillating input electrical signal to said colloidal suspension, and extracting a first output current from said colloidal suspension, and applying said input signal to a reference solution which is substantially identical to said colloidal suspension except that said colloidal particles are removed, and extracting a second output current from said reference solution;

deriving a differential output current by subtracting said second output current from said first output current;

measuring the magnitude of said differential output current; and comparing the phase of said differential output current to the phase of said input signal to determine the difference in phase between said differential output current and said input signal.

2. The method of claim 1, wherein said input signal has a frequency between about 1 Hz and 10 Hz.

3. For a toner suspension having a liquid medium, charge control agent, and a plurality of toner particles dispersed throughout said medium, a method for determining the quality of said toner suspension, comprising the steps of:

applying an oscillating input electrical signal to said toner suspension, and extracting a first output current from said toner suspension, and applying said input signal to a reference solution which is substantially identical to said toner suspension except that said toner particles are removed, and extracting a second output current from said reference solution;

deriving a differential output current by subtracting said second output current from said first output current;

measuring the magnitude of said differential output current; and comparing the phase of said differential output current to the phase of said input signal to determine the difference in phase between said differential output current and said input signal.

4. The method of claim 3, wherein said input signal has a frequency between about 1 Hz and 10 Hz.

5. For a colloidal suspension having colloidal particles dispersed throughout a continuous medium, an apparatus for determining the quality of said colloidal suspension, comprising:

an oscillating signal source for generating an oscillating input electrical signal;

a test cell for housing said colloidal suspension having an input electrode for receiving said input signal, and an output electrode for outputting a first output current, both said input and output electrodes electrically coupled to said colloidal suspension;

a reference cell for housing a reference solution which is substantially identical to said colloidal suspension except that said colloidal particles are removed, said reference cell having a second input electrode for receiving said input signal, and a second output electrode for outputting a second output current, both said second input and output electrodes electrically coupled to said reference solution;

a differential amplifier having two inputs for receiving said first and second output currents, and an output for providing a differential output current;

a magnitude detector for measuring the magnitude of said differential output current; and a phase detector having two inputs for receiving said differential output current and said input signal for measuring the difference in phase between said differential output current and said input signal.

6. The apparatus of claim 5, wherein said input signal has a frequency between about 1 Hz and 10 Hz.

7. The apparatus of claim 5, wherein said reference cell comprises:
a hollow casing having a first open end and a second open end, said reference solution residing within the hollow portion of said casing;
a first end cap for covering said first open end;
a second end cap for covering said second open end;
a first electrode attached to said casing and residing within the hollow portion of said casing; and
a second electrode having two ends, each end attached to one of said end caps, said second electrode residing within the hollow portion of said casing.

8. The apparatus of claim 7, wherein said first electrode is a hollow conductor having sufficiently large dimensions to accommodate said second electrode within the hollow portion of said hollow conductor.

9. The apparatus of claim 5, wherein said reference cell comprises:
a hollow casing having a first open end and a second open end, said reference solution residing within the hollow portion of said casing;
a first end cap for covering said first open end;
a second end cap for covering said second open end;
a first electrode attached to said first end cap, said first electrode residing within the hollow portion of said casing; and
a second electrode attached to said second end cap, said second electrode residing within the hollow portion of said casing.

10. The apparatus of claim 9, wherein said first electrode is a hollow conductor having sufficiently large dimensions to accommodate said second electrode within the hollow portion of said hollow conductor.

11. The apparatus of claim 5, wherein said test cell comprises:
a hollow casing having a first open end, a second open end, and at least one hole within close proximity of said first open end, said colloidal suspension residing within the hollow portion of said casing;
an end cap for covering said first open end without obstructing said hole;
a first electrode attached to said casing and residing within the hollow portion of said casing; and
a second electrode having one end attached to said end cap, said second electrode residing within the hollow portion of said casing.

12. The apparatus of claim 11, wherein said first electrode is a hollow conductor having sufficiently large dimensions to accommodate said second electrode within the hollow portion of said hollow conductor.

13. The apparatus of claim 5, wherein said test cell comprises:
a hollow casing having a first open end and a second open end, said colloidal suspension residing within the hollow portion of said casing;
a first end cover having a hollow extension for partially covering said first open end;
a second end cover having a hollow extension for partially covering said second open end;
a first electrode attached to said first end cover, said first electrode residing within the hollow portion of said casing; and
a second electrode attached to said second end cover, said second electrode residing within the hollow portion of said casing.

14. The apparatus of claim 13, wherein said first electrode is a hollow conductor having sufficiently large dimensions to accommodate said second electrode within the hollow portion of said hollow conductor.

15. For a toner suspension having a liquid medium, charge control agent, and a plurality of toner particles dispersed throughout said medium, an apparatus for determining the quality of said toner suspension, comprising:
an oscillating signal source for generating an oscillating input electrical signal;
a test cell for housing said toner suspension having an input electrode for receiving said input signal, and an output electrode for outputting a first output current, both said input and output electrodes electrically coupled to said toner suspension;
a reference cell for housing a reference solution which is substantially identical to said toner suspension except that said toner particles are removed, said reference cell having a second input electrode for receiving said input signal, and a second output electrode for outputting a second output current, both said second input and output electrodes electrically coupled to said reference solution;
a differential amplifier having two inputs for receiving said first and second output currents, and an output for providing a differential output current;
a magnitude detector for measuring the magnitude of said differential output current; and
a phase detector having two inputs for receiving said differential output current and said input signal for measuring the difference in phase between said differential output current and said input signal.

16. The apparatus of claim 15, wherein said input signal has a frequency between about 1 Hz and 10 Hz.

17. The apparatus of claim 15, wherein said reference cell comprises:
a hollow casing having a first open end and a second open end, said reference solution residing within the hollow portion of said casing;
a first end cap for covering said first open end;
a second end cap for covering said second open end;
a first electrode attached to said casing and residing within the hollow portion of said casing; and
a second electrode having two ends, each end attached to one of said end caps, said second electrode residing within the hollow portion of said casing.

18. The apparatus of claim 17, wherein said first electrode is a hollow conductor having sufficiently large dimensions to accommodate said second electrode within the hollow portion of said hollow conductor.

19. The apparatus of claim 15, wherein said reference cell comprises:
a hollow casing having a first open end and a second open end, said reference solution residing within the hollow portion of said casing;
a first end cap for covering said first open end;
a second end cap for covering said second open end;
a first electrode attached to said first end cap, said first electrode residing within the hollow portion of said casing; and a second electrode attached to said second end cap, said second electrode residing within the hollow portion of said casing.

20. The apparatus of claim 19, wherein said first electrode is a hollow conductor having sufficiently large dimensions to accommodate said second electrode within the hollow portion of said hollow conductor.

21. The apparatus of claim 15, wherein said test cell comprises:
   a hollow casing having a first open end, a second open end, and at least one hole within close proximity of said first open end, said toner suspension residing within the hollow portion of said casing;
   an end cap for covering said first open end without obstructing said hole;
   a first electrode attached to said casing and residing within the hollow portion of said casing; and
   a second electrode having one end attached to said end cap, said second electrode residing within the hollow portion of said casing.

22. The apparatus of claim 21, wherein said first electrode is a hollow conductor having sufficiently large dimensions to accommodate said second electrode within the hollow portion of said hollow conductor.

23. The apparatus of claim 15, wherein said test cell comprises:
   a hollow casing having a first open end and a second open end, said toner suspension residing within the hollow portion of said casing;
   a first end cover having a hollow extension for partially covering said first open end;
   a second end cover having a hollow extension for partially covering said second open end;
   a first electrode attached to said first end cover, said first electrode residing within the hollow portion of said casing; and
   a second electrode attached to said second end cover, said second electrode residing within the hollow portion of said casing.

24. The apparatus of claim 23, wherein said first electrode is a hollow conductor having sufficiently large dimensions to accommodate said second electrode within the hollow portion of said hollow conductor.

* * * * *